United States Patent [19]

Argyropoulos et al.

[11] Patent Number: 5,420,341

[45] Date of Patent: May 30, 1995

[54] HINDERED-HYDROXYL FUNCTIONAL (METH)ACRYLATE COMPOUNDS AND PROCESSES FOR THE PREPARATION THEREOF

[75] Inventors: John N. Argyropoulos, Scott Depot; Brian L. Hilker, Winfield; Joseph V. Koleske, Charleston, all of W. Va.; Jefrey M. O. Lewis, Farmington Hills, Mich.

[73] Assignee: Union Carbide Chemicals & Plastics, Danbury, Conn.

[21] Appl. No.: 962,559

[22] Filed: Oct. 19, 1992

[51] Int. Cl.⁶ ............................................. C07C 69/52
[52] U.S. Cl. ............................................. 560/224
[58] Field of Search ............................................. 560/224

[56] References Cited

U.S. PATENT DOCUMENTS

| | | | |
|---|---|---|---|
| 2,458,888 | 1/1949 | Rehberg et al. | 260/83 |
| 2,499,848 | 3/1950 | Catlin et al. | 260/485 |
| 3,367,966 | 2/1968 | Knopf et al. | 260/494 |
| 3,387,022 | 6/1968 | Hagemeyer et al. | 260/486 |
| 3,390,115 | 6/1968 | Hagemeyer, Jr. et al. | 260/31.6 |
| 4,110,539 | 8/1978 | Albers et al. | 560/240 |
| 4,225,726 | 9/1980 | Morris et al. | 560/238 |
| 4,804,581 | 2/1989 | Geary et al. | 428/332 |
| 4,988,766 | 1/1991 | Das et al. | 525/123 |
| 5,068,288 | 11/1991 | Taijan et al. | 525/155 |

FOREIGN PATENT DOCUMENTS

| | | | |
|---|---|---|---|
| 2604912 | 8/1977 | Germany. | |
| 1092884 | 11/1967 | United Kingdom | C08F 15/00 |
| 1110033 | 4/1968 | United Kingdom | C08F 15/00 |

OTHER PUBLICATIONS

STN International Registry File Search Results—P162427C and P162246K, American Chemical Society, Jun. 1992.

CA 111:154520 (4) 1989.

*Primary Examiner*—Paul J. Killos
*Attorney, Agent, or Firm*—R. M. Allen

[57] ABSTRACT

This invention relates to hindered-hydroxyl functional (meth)acrylate compounds and derivatives thereof and to processes for the preparation thereof. The hindered-hydroxyl functional (meth)acrylate compounds and derivatives thereof are useful alone or in the production of intermediates, and have utility in coatings, adhesives, inks, sealants, reactive surfactants, wet adhesion monomers, as well as in other end uses.

1 Claim, No Drawings

HINDERED-HYDROXYL FUNCTIONAL (METH)ACRYLATE COMPOUNDS AND PROCESSES FOR THE PREPARATION THEREOF

RELATED APPLICATIONS

The following are related, commonly assigned applications, filed on an even date herewith:

U.S. patent application Ser. No. 07/962,561, and U.S. patent application Ser. No. 07/963,213, (now U.S. Pat. No. 5,290,602, granted Mar. 1, 1994); both of which are incorporated herein by reference.

BRIEF SUMMARY OF THE INVENTION

1. Technical Field

This invention relates to hindered-hydroxyl functional (meth)acrylate compounds and to processes for the preparation thereof. The hindered-hydroxyl functional (meth)acrylate compounds are particularly useful as copolymerizable monomers in various polymerization methods.

2. Background of the Invention

Although (meth)acrylic coatings are known to have very good weathering characteristics, they are subject to deterioration by etching under both high and low pH conditions. Such etching first manifests itself as permanent spotting which is unpleasing to the eye. After a period of time that is often dependent on temperature, there is removal or other deterioration of the coating in the spotted areas and then further deterioration in other areas and finally failure of the coating in a functional sense. Such etching takes place during the drying of droplets of water containing relatively small amounts of acidic or alkaline moieties from the substrate. As the droplet decreases in volume, the pH decreases to very low values in the case of acid moieties and increases to very high values in the case of alkaline moieties. Under these conditions, relatively rapid attack of the substrate occurs.

The coatings industry is actively seeking coatings with improved hydrolytic resistance particularly at high and low pH values over that of the current acrylics. Such improved resistance would result in coatings that have enhanced resistance to hostile environment as such as those caused by acid rain, by air-borne chemicals, and by cleaners used for dirt removal.

Another need in the field of coatings is low viscosity coating formulations that will allow higher application solids to be achieved and maintain or improve final cured coating performance characteristics. The requirement for such high solids coating formulations is driven by both federal and state regulations as well as a desire to decrease any impact volatile organic solvents may have on the environment. Coatings that have high solids can have an unbalanced property profile that is usually related to the low molecular weight oligomers/polymers that must be used to obtain a sufficiently low viscosity in formulated coating systems that have low volatile organic content. Coatings with high solids, low volatile organic content, and improved physical and chemical characteristics result in a decreased environmental impact caused by volatile solvents, decreased energy requirements for volatile solvent manufacture and volatilization, and a longer service life which requires less replacement and thus conserves both energy and natural resources.

DISCLOSURE OF THE INVENTION

This invention relates to hindered-hydroxyl functional meth(acrylate) compounds represented by the formula:

$$R_1R_2C\!=\!C(R_3)\!-\!C(O)\!-\!O\!-\!R_4 \qquad (I)$$

wherein:

$R_1$, $R_2$ and $R_3$ are the same or different and are hydrogen or a substituted or unsubstituted monovalent hydrocarbon residue, preferably an alkyl group of 1 to 3 carbon atoms;

$R_4$ is a substituted or unsubstituted monovalent hydrocarbon residue represented by the formula:

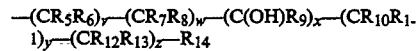

$$-(CR_5R_6)_v\!-\!(CR_7R_8)_w\!-\!(C(OH)R_9)_x\!-\!(CR_{10}R_{11})_y\!-\!(CR_{12}R_{13})_z\!-\!R_{14}$$

wherein:

each $R_5$, $R_6$, $R_7$, $R_8$, $R_9$, $R_{10}$, $R_{11}$, $R_{12}$ and $R_{13}$ are the same or different and are hydrogen or a substituted or unsubstituted monovalent hydrocarbon residue;

$R_{14}$ is hydrogen, hydroxyl or a substituted or unsubstituted monovalent hydrocarbon residue provided $R_{14}$ is hydroxyl when x is value of 0 and $R_{14}$ is other than hydroxyl when x is a value of 1;

each of v, w, y and z is a value of from 0 to about 5 and the sum of v+w+x+y+z is a value of from about 3 to about 15; and x is a value of 0 or 1;

provided (i) at least one of w and y is a value other than 0 when x is a value of 1; (ii) at least one of $R_7$, $R_8$, $R_9$, $R_{10}$ and $R_{11}$ is other than hydrogen when x is a value of 1; and (iii) at least one of $R_{12}$ and $R_{13}$ is other than hydrogen when x is a value of 0.

This invention also relates to processes for preparing hindered-hydroxyl functional (meth)acrylate compounds.

DETAILED DESCRIPTION

The hindered-hydroxyl functional (meth)acrylate compounds of this invention can be prepared, for example, by (i) direct esterification of appropriate diol compound with methacrylic acid or acrylic acid, (ii) reaction of appropriate diol compound with methacrylic anhydride or acrylic anhydride, and (iii) transesterification of appropriate diol compound with alkyl methacrylate or alkyl acrylate, e.g., methyl methacrylate, methyl acrylate, ethyl methacrylate, ethyl acrylate, propyl methacrylate, propyl acrylate, and the like.

The direct esterification of appropriate diol compound with methacrylic acid or acrylic acid can be conducted at a temperature of from about 100° C. to 300° C. for a period of about 1 hour to about 7 days with the longer time being used at the lower temperature, preferably from about 125° C. to about 200° C. 1 hour to about 5 days, and more preferably at about 125° C. to 150° C. for about 1 hour to about 48 hours. Direct esterifications are often carried out at reflux temperature which is dependent on the boiling point temperature of the solvent used for a period of about 6 to about 8 hours. Suitable solvents include benzene, xylene, toluene and the like. One or more stabilizers such as hydroquinone, methoxyhydroquinone, phenothiazine and the like should be used to prevent polymerization.

The direct esterification reaction can be conducted over a wide range of pressures ranging from atmospheric pressure to superatmospheric pressures, e.g., from about 1 atmosphere to about 100 atmospheres or greater. It is preferable to conduct the direct esterification reaction at pressures of from about atmospheric to about 25 atmospheres. The direct esterification reaction is preferably effected in the liquid or vapor states or mixtures thereof.

The molar ratio of appropriate diol compound to methacrylic acid or acrylic acid in the direct esterification reaction is not narrowly critical and can range from about 0.05:1 or less to about 50:1 or greater, preferably from about 0.1:1 to about 10:1.

The reaction of appropriate diol compound with methacrylic anhydride or acrylic anhydride can be conducted at a temperature of from about 0° C. to 150° C. for a period of about 1 hour to about 7 days with the longer time being used at the lower temperature, preferably from about 15° C. to about 100° C. for about 1 hour to about 5 days, and more preferably at about 25° C. to 50° C. for about 1 hour to about 48 hours. One or more stabilizers such as hydroquinone, methoxyhydroquinone, phenothiazine, and the like should be used to prevent polymerization.

The reaction of appropriate diol compound with methacrylic anhydride or acrylic anhydride can be conducted over a wide range of pressures ranging from atmospheric pressure to superatmospheric pressures, e.g., from about 1 atmosphere to about 100 atmospheres or greater. It is preferable to conduct the reaction at pressures of from about atmospheric to about 25 atmospheres. The reaction is preferably effected in the liquid or vapor states or mixtures thereof.

The molar ratio of appropriate diol compound to methacrylic anhydride or acrylic anhydride in the reaction is not narrowly critical and can range from about 0.05:1 or less to about 50:1 or greater, preferably from about 0.1:1 to about 10:1.

The transesterification of appropriate diol compound with alkyl methacrylate or alkyl acrylate can be conducted at a temperature of from about −20° C. to 250° C. for a period of about 10 minutes to about 7 days with the longer time being used at the lower temperature, preferably from about 0° C. to about 200° C. for about 1 hour to about 5 days, and more preferably at about 0° C. to 180° C. for about 1 hour to about 48 hours. One or more stabilizers such as hydroquinone, methoxyhydroquinone, phenothiazine and the like should be used to prevent polymerization.

The transesterification reaction can be conducted over a wide range of pressures ranging from atmospheric pressure to superatmospheric pressures, e.g., from about 1 atmosphere to about 100 atmospheres or greater. It is preferable to conduct the transesterification reaction at pressures of from about atmospheric to about 25 atmospheres. The transesterification reaction is preferably effected in the liquid or vapor states or mixtures thereof.

The molar ratio of appropriate diol compound to alkyl methacrylate or alkyl acrylate in the transesterification reaction is not narrowly critical and can range from about 0.05:1 or less to about 50:1 or greater, preferably from about 0.1:1 to about 10:1.

Illustrative of suitable diol compounds useful in the processes of this invention include, for example, 2-ethyl-1,3-hexanediol, 2-methyl-1,3-pentanediol, 2-propyl-1,3-heptane diol, 2-ethyl-1,3-heptane diol, 2-ethyl-1,3-propane diol, 2-i-propyl-3-i-butyl-1,3-propane diol, 2-i-propyl-3-methyl-1,3-propane diol, 1-i-butyl-1,3-propane diol, 1-methyl-2-butyl-1,3-propane diol, 2,2,4-trimethyl-1,3-pentane diol, and the like. Preferred hindered-hydroxyl functional (meth)acrylate compounds of this invention are obtained from 2,2,4-trimethyl-1,3-pentane diol, 2-methyl-1,3-pentane diol and 2-ethyl-1,3-hexane diol. The diol compounds can be prepared by conventional methods such as aldol condensations, the reaction of formaldehyde with ketones, or other suitable methods.

Optionally the transesterification reaction mass may contain a transesterification catalyst. Illustrative of suitable transesterification catalysts are potassium bicarbonate, sodium bicarbonate, potassium thiocyanate, barium thiocyanate, calcium triocyanate, cobalt thiocyanate, sodium thiocyanate, zinc thiocyanate, other salts of weak acids such as sodium acetate, lithium acetate, calcium acetate, zinc acetate, and other metal salts of acetic acid and carbonic acid, alkali metal alkoxides such as sodium methoxide, potassium methoxide, lithium methoxide, zinc methoxide, calcium methoxide, metal oxalates, and the like. When used, the catalysts can be present in amounts of from about 0.10 mole percent or less to 20 mole percent with it preferred that from about 0.20 mole percent to about 10 mole percent be used. The transesterification catalyst may be added to the reaction mass all at one time, in discrete portions that may be of the same or different size, or in a continuous uniform or non uniform manner over the entire reaction time period or over a portion of the reaction time period.

The products produced by the processes of this invention include hindered-hydroxyl functional (meth)acrylate compounds, in particular, those hindered-hydroxyl functional (meth)acrylate compounds encompassed within Formula I above. These products are useful in a number of ways including imparting excellent physical characteristics, such as water resistance, chemical resistance, resistance to hostile environments such as acid rain, and the like, to coatings, inks, adhesives, and sealants prepared from the hindered-hydroxyl functional (meth)acrylate compounds or derivatives thereof, and as reactive surfactants.

Illustrative hindered-hydroxyl functional (meth)acrylate compounds prepared by the processes of this invention include, for example, 2-ethyl-3-hydroxyhexyl methacrylate, 1-propyl-2-ethyl-3 hydroxypropyl methacrylate, 1-ethyl-2-methyl-3-hydroxypropyl methacrylate, 2-methyl-3-hydroxypentyl methacrylate, 2-propyl-3-hydroxyheptyl methacrylate, 1-butyl-2-propyl-3-hydroxypropyl methacrylate, 2-ethyl-3-hydroxyheptyl methacrylate, 1-butyl-2-ethyl-3-hydroxypropyl methacrylate, 2-propyl-3-hydroxypropyl methacrylate, 2-ethyl-3-hydroxypropyl methacrylate, 1-i-butyl-2-i-propyl-3-hydroxypropyl methacrylate, 2-i-propyl-3-hydroxy-5-methylhexyl methacrylate, 1-methyl-2-i-propyl-3-hydroxypropyl methacrylate, 2-i-propyl-3-methyl-3-hydroxypropyl acrylate, 1-i-butyl-3-hydroxypropyl methacrylate, 3-hydroxy-5-methylhexyl methacrylate, 1-methyl-2-butyl-3-hydroxypropyl methacrylate, 2-butyl-3-hydroxybutyl methacrylate, 1-i-propyl-2,2-dimethyl-3-hydroxypropyl methacrylate, 2,2-dimethyl-3-hydroxy-4-methylpentyl methacrylate, and the like.

For purposes of Formula I above, the following compounds defined in (a) through (r) are outside the scope of claim 1 of this invention:

(a) when v, w and z are each a value of 1, x and y are each a value of 0, $R_1$, $R_2$, $R_5$, $R_6$, $R_7$ and $R_8$ are each hydrogen, $R_3$ is hydrogen or methyl, and $R_{14}$ is hydroxyl, then at least one of $R_{12}$ and $R_{13}$ is other than hydrogen or methyl;

(b) when v and z are each a value of 1, w, x and y are each a value of 0, $R_1$ and $R_2$ are each hydrogen, $R_3$ is hydrogen or methyl, one of $R_5$ and $R_6$ is methyl and the other is hydrogen, and $R_{14}$ is hydroxyl, then at least one of $R_{12}$ and $R_{13}$ is other than hydrogen or methyl;

(c) when y and z are each a value of 1, v, w and x are each a value of 0, $R_1$ and $R_2$ are each hydrogen, $R_3$ is hydrogen or methyl, $R_{10}$ and $R_{11}$ are each methyl, and $R_{14}$ is hydroxyl, then at least one of $R_{12}$ and $R_{13}$ is other than hydrogen or methyl;

(d) when w, y and z are each a value of 1, v and x are each a value of 0, $R_1$, $R_2$, $R_{10}$ and $R_{11}$ are each hydrogen, $R_3$ is hydrogen or methyl, one of $R_7$ and $R_8$ is methyl and the other is hydrogen, and $R_{14}$ is hydroxyl, then at least one of $R_{12}$ and $R_{13}$ is other than hydrogen or methyl;

(e) when v, w and z are each a value of 1, y is a value of 2, x is a value of 0, $R_1$, $R_2$, $R_3$, $R_5$, $R_6$, $R_7$, $R_8$, $R_{10}$ and $R_{11}$ are each hydrogen, and $R_{14}$ is hydroxyl, then at least one of $R_{12}$ and $R_{13}$ is other than hydrogen or methyl;

(f) when v, w, y and z are each a value of 1, x is a value of 0, $R_1$, $R_2$, $R_5$, $R_6$, $R_7$, $R_8$, $R_{10}$ and $R_{11}$ are each hydrogen, $R_3$ is methyl, and $R_{14}$ is hydroxyl, then at least one of $R_{12}$ and $R_{13}$ is other then hydrogen or ethyl;

(g) when v, w and z are each a value of 1, x and y are each a value of 0, $R_1$, $R_2$, $R_3$, $R_7$ and $R_8$ are each hydrogen, $R_5$ and $R_6$ are each methyl, and $R_{14}$ is hydroxyl, then at least one of $R_{12}$ and $R_{13}$ is other than hydrogen or methyl;

(h) when v, w, y and z are each a value of 1, x is a value of 0, $R_1$, $R_2$, $R_3$, $R_7$, $R_8$, $R_{10}$ and $R_{11}$ are each hydrogen, one of $R_5$ and $R_6$ is methyl and the other is hydrogen, and $R_{14}$ is hydroxyl, then at least one of $R_{12}$ and $R_{13}$ is other than hydrogen or methyl;

(i) when v, w and z are each a value of 1, x and y are each a value of 0, $R_1$, $R_2$, $R_3$, $R_7$ and $R_8$ are each hydrogen, $R_5$ and $R_6$ are each methyl, and $R_{14}$ is hydroxyl, then at least one of $R_{12}$ and $R_{13}$ is other than hydrogen or methyl;

(j) when v and z are each a value of 1, w, x and y are each a value of 0, $R_1$, $R_2$, $R_5$ and $R_6$ are each hydrogen, $R_3$ is hydrogen or methyl, and $R_{14}$ is hydroxyl, then at least one of $R_{12}$ and $R_{13}$ is other than hydrogen or phenyl;

(k) when v, w and z are each a value of 1, x and y are each a value of 0, $R_1$, $R_2$, $R_5$ and $R_6$ are each hydrogen, $R_3$, $R_7$ and $R_8$ are each methyl, and $R_{14}$ is hydroxyl, then at least one of $R_{12}$ and $R_{13}$ is other than hydrogen or propyl;

(l) when v, w, x and z are each a value of 1, y is a value of 0, $R_1$, $R_2$, $R_5$, $R_6$ and $R_9$ are each hydrogen, $R_3$ is hydrogen or methyl, and $R_7$ and $R_8$ are each methyl, then at least one of $R_{12}$, $R_{13}$ and $R_{14}$ is other than hydrogen or methyl;

(m) when v, w, y and z are each a value of 1, x is a value of 0, $R_1$, $R_2$, $R_3$, $R_7$, $R_8$, $R_{10}$ and $R_{11}$ are each hydrogen, $R_5$ and $R_6$ are each methyl, and $R_{14}$ is hydroxyl, then at least one of $R_{12}$ and $R_{13}$ is other than hydrogen or methyl;

(n) when v, w and z are each a value of 1, y is a value of 3, x is a value of 0, $R_1$, $R_2$, $R_5$, $R_6$, $R_7$, $R_8$, $R_{10}$ and $R_{11}$ are each hydrogen, $R_3$ is methyl, and $R_{14}$ is hydroxyl, then at least one of $R_{12}$ and $R_{13}$ is other than hydrogen or ethyl;

(o) when v and z are each a value of 1, w, x and y are each a value of 0, $R_1$, $R_2$, $R_3$, $R_5$ and $R_6$ are each hydrogen, and $R_{14}$ is hydroxyl, then at least one of $R_{12}$ and $R_{13}$ is other than hydrogen, ethyl or butyl;

(p) when w, x and z are each a value of 1, v and y are each a value of 0, $R_1$, $R_2$, $R_3$, $R_7$, $R_8$ and $R_9$ are each hydrogen, then at least one of $R_{12}$, $R_{13}$ and $R_{14}$ is other than hydrogen or phenyl;

(q) when v and z are each a value of 1, w, x and y are each a value of 0, $R_1$, $R_2$, $R_3$, $R_5$ and $R_6$ are each hydrogen, and $R_{14}$ is hydroxyl, then at least one of $R_{12}$ and $R_{13}$ is other than hydrogen, methyl or phenyl; and (r) when v, w and z are each a value of 1, y is a value of 9, x is a value of 0, $R_1$, $R_2$, $R_3$, $R_5$, $R_6$, $R_7$, $R_8$, $R_{10}$ and $R_{11}$ are each hydrogen, and $R_{14}$ is hydroxyl, then at least one of $R_{12}$ and $R_{13}$ is other than hydrogen or methyl.

The hindered-hydroxyl functional (meth)acrylate compounds produced by the processes of this invention can be separated by distillation. For example, a crude reaction product can be subjected to a distillation-separation at atmospheric or reduced pressure through a packed distillation column. Reactive distillation may be useful in conducting certain reactions of this invention.

The processes of this invention may be carried out using, for example, a fixed bed reactor, a fluid bed reactor, or a slurry reactor. The optimum size and shape of the catalysts will depend on the type of reactor used. In general, for fluid bed reactors, a small, spherical catalyst particle is preferred for easy fluidization. With fixed bed reactors, larger catalyst particles are preferred so the back pressure within the reactor is kept reasonably low.

The processes of this invention can be conducted in a batch or continuous fashion, with recycle of unconsumed starting materials if required. The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials. When complete conversion is not desired or not obtainable, the starting materials can be separated from the product, for example by distillation, and the starting materials then recycled back into the reaction zone.

The processes are conducted for a period of time sufficient to produce the hindered-hydroxyl functional (meth)acrylate compounds. The exact reaction time employed is dependent, in part, upon factors such as temperature, nature and proportion of starting materials, and the like. The reaction time will normally be within the range of from about one-half to about 100 hours or more, and preferably from less than about one to about ten hours.

The process may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

The hindered-hydroxyl functional (meth)acrylate compounds produced by the processes of this invention can undergo further reaction(s) to afford desired derivatives thereof. Such permissible derivatization reactions can be carried out in accordance with conventional procedures known in the art. Illustrative derivatization reactions include, for example, esterification, etherification, alkoxylation, amination, alkylation, hydrogenation, dehydrogenation, reduction, acylation, condensation, carboxylation, carbamoylation, oxidation, silylation and the like, including permissible combinations thereof. This invention is not intended to be limited in any manner by the permissible derivatization reactions or permissible derivatives of hindered-hydroxyl functional (meth)acrylate compounds.

More particularly, the hindered-hydroxyl functional (meth)acrylate compounds of this invention can undergo any of the known reactions of hydroxyl groups illustrative of which are reactions with acyl halides to form esters; with ammonia, a nitrile, or hydrogen cyanide to form amines; with alkyl acid sulfates to form disulfates; with carboxylic acids and acid anhydrides to form esters and polyesters; with alkali metals to form salts; with ketenes to form esters; with acid anhydrides to form carboxylic acids; with oxygen to form aldehydes and carboxylic acids; ring-opening reactions with lactones, tetrahydrofuran, and alkylene oxides such as ethylene oxide, propylene oxide, epichlorohydrin; dehydrogenation to form aldehydes, isocyanates to form urethanes, and the like.

The hindered hydroxyl-functional (meth)acrylate compounds of the invention are useful in the formation of intermediates such as copolymers/oligomers/polymers for formulation with crosslinking agents; for preparation of alkylene oxide and lactone adducts that are useful as surfactants and/or intermediates; for preparation of urethane (meth)acrylates; for preparation of carboxyl-terminated, carbamoyl-terminated, and isocyanate-terminated (meth)acrylate adducts; and the like.

For purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

As used herein, the term "substituted" is contemplated to include all permissible substituents of organic compounds unless otherwise indicated. In a broad aspect, the permissible substituents include acyclic and cyclic, branched and unbranched, carbocyclic and heterocyclic, aromatic and nonaromatic substituents of organic compounds. Illustrative substituents include, for example, alkyl, alkyloxy, aryl, aryloxy, hydroxy, hydroxyalkyl, amino, aminoalkyl, halogen and the like in which the number of carbons can range from 1 to about 20 or more, preferably from 1 to about 12. The permissible substituents can be one or more and the same or different for appropriate organic compounds. This invention is not intended to be limited in any manner by the permissible substituents of organic compounds.

As used herein, the molecular weights were determined by gel permeation chromatography using polystyrene calibration standards.

Certain of the following examples are provided to further illustrate this invention.

GLOSSARY OF TERMS

Aminoplast 1—A hexamethoxymelamine commercially available from American Cyanamid as Cymel ® 303.

Aminoplast 2—A methylated/butylated melamine commercially available from Monsanto Company as Resimene ® 755.

Blocked Isocyanate 1—A blocked isocyanate, that is thought to be a methyl ethyl ketone oxime blocked trimer of 4,4'-dicyclohexanemethyl diisocyante, commercially available from Miles, Inc. under the designation Desmodur BL-3174A.

Catalyst 1—A 40% by weight solution of para-toluene sulfonic acid in methanol.

Catalyst 2—Dibutyltin dilaurate.

Surfactant 1—A 25% by weight solution in methyl amyl ketone of a silicone-based surfactant commercially available from Union Carbide Chemicals and Plastics Company Inc. as Silwet ® L-7001.

Surfactant 2—A 25% by weight solution in methyl amyl ketone of a silicone-based surfactant commercially available from Union Carbide Chemicals and Plastics Company Inc. as Silwet ® L-77.

Photoinitiator 1—An aryl sulfonium hexafluoroantimonate photoinitiator that is commercially available from Union Carbide Chemicals and Plastics Company Inc. as Cyracure ® UVI-6974.

Double Rubs—Solvent resistance was measured as the number of solvent (methyl ethyl ketone double rubs or acetone double rubs) that were required to cut through the coating. If 100 rubs or more did not cut through the coating, the coating was recorded as >100. To perform the test, the solvent-soaked cloth was rubbed back and forth with hand pressure. A rub back and forth was designated as one "double rub."

Crosshatch Adhesion—Procedure conducted in accordance with ASTM D 3359-87.

Pencil Hardness—Procedure conducted in accordance with ASTM D 3363-74.

60° Gloss—Procedure conducted in accordance with ASTM D 523.

20° Gloss—Procedure conducted in accordance with ASTM D 523.

Impact Resistance. Procedure conducted in accordance with ASTM D 2794-84.

Acid etch resistance—A Fini automatic transfer pipette was used to place a series of 50 micro-liter droplets of sulfuric acid solution at approximately ¼-inch intervals in two rows along the length of one or more coated panels. Usually two panels were required to provide the length of surface needed to examine the temperature range of 40° to 100° C. that were achieved in the gradient temperature oven. Two rows of spots were used for duplication of the test. The coated panels were placed in an end-to-end position on the heating bank of a BYK Chemie gradient temperature oven and the first spots were aligned with the #1 rod which was a 40° C. which resulted in the various spots being at temperatures that ranged to 100° C. The sulfuric acid solution droplets, which were of indicated acidity, were allowed to contact the coating for various times at the indicated temperatures. After the desired heating time, the panels were removed from the gradient oven, cooled to room temperature, rinsed thoroughly with distilled water, lightly patted dry, and evaluated.

Evaluation was accomplished by examining the areas that had been covered with the droplets with a 10-power, lighted magnifier. The following points of comparison were observed and recorded for each coating.

a) The lowest temperature spot area with a visible defect in the coating. A "visible defect" is the first sign of any blush, bubbling, yellowing, or other visible change.

b) The lowest temperature spot with a severe defect. A "severe defect" is blistering or complete removal of the coating with the substrate visible. This latter factor means the acidic solution has cut though the coating to the substrate.

c) A scaled 1 to 5 rating of any defect or change occurring specifically in the 50° C., 60° C., and 70° C. areas of the coating using the following rating system.

1—Fail. Coating is cut to the substrate or has severe bubbling.

2—Severe. Small blister or bubble present in the coating.

3—Moderate. Pinhole defect or slight change in surface of coating by fingertip feeling or visible loss of gloss.

4—Slight. Blushing or yellowing of coating with no change by fingertip feeling.

5—Unchanged. No visible evidence of any effect.

EXAMPLES

Preparation A. A methacrylate ester of 2,2,4-trimethyl-1,3-pentanediol was prepared by placing 1800 grams (12.33 moles) of 2,2,4-trimethyl-1,3-pentanediol (TMPD) in a four-neck, glass reaction flask equipped with a Therm-O-Watch temperature control device, a nitrogen inlet and outlet, a stirrer, and a feeding port. The TMPD was melted and dried by heating to 85° C. while flowing dry nitrogen through the reactor for 2 hours. Then 4.0 grams of methoxyhydroquinone, 4.0 gram of phenothiazine, and 2,277 grams (14.79 moles) of freshly distilled methacrylic anhydride were added. While stirring and employing a nitrogen purge, 81.0 grams of distilled pyridiene were added and the reaction mass was heated to and held at 35° C. for 1-2 days after which time gas chromatographic analysis indicated that the reaction was complete. Excess methacrylic anhydride was quenched by first adding methanol, and these reaction products as well as methacrylic acid formed during the desired alkylmethacrylate ester formation were removed by washing with water. Gas chromatography, mass spectrometry, and Fourier-transform infrared analyses indicated that both monomethacrylate isomers and the expected diacrylate had formed. The monomethacrylates were separated from the diacrylate by fractional distillation.

Example 1 and Control Examples A and B. Example 1 copolymer/oligomer was prepared from a 300-gram mixture of the Preparation A alkyl monomethacrylate mixture, butyl acrylate, and methyl methacrylate. For comparison purposes, mixtures containing hydroxyethyl methacrylate (Control A) or hydroxypropyl methacrylate (Control B) were used in the same molar amount as the Preparation A methacrylate of Example 1 and approximately equal amounts of butyl acrylate and methyl methacrylate so the total amount of monomer mixture equaled about 300 grams. A chain transfer agent, 3-mercapto-1-propanol, was included in the monomer mixture. The initial pentyl propionate solvent was placed in a 2-liter, four-neck, glass reaction flask equipped with a mechanical stirrer, a Thermo-watch heat controller, a nitrogen sparger, a water-cooled condenser, and 500-milliliter and 125-milliliter addition funnels. A nitrogen sparge was maintained throughout the procedure. The solvent was heated to 125° C., and the monomer mixture was fed by means of a piston pump to the flask over a four-hour period while controlling the temperature at 125° C. Concurrently, the initiator mixture consisting of t-amyl peroxyacetate (Lupersol 555M60) initiator dissolved in pentyl propionate was fed to the reaction flask via a second piston pump over the same time period. The two feeds were introduced into the reactor below the liquid surface and from opposite sides of the reactor. After completion of the feeding step, the monomer line was flushed with pentyl propionate and the reaction was allowed to proceed for 30 minutes at 125° C. Then a second initiator feed consisting of a mixture of t-amyl peroxyacetate dissolved in pentyl propionate was fed to the reaction mass and the reaction was allowed to proceed for an additional 2 hours at 125° C. The solution of copolymer was then cooled to room temperature and analyzed by gel permeation chromatography using polystyrene standards to determine relative average molecular weights, for total solids content, and for viscosity. The results indicated that Example 1 copolymer/oligomer prepared from Preparation A hydroxyalkyl methacrylate had a lower molecular weight and lower viscosity (Brookfield viscosity), characteristics which allow preparation of higher total solids coating formulations, than Control Examples A and B copolymers/oligomers.

| | | Control Examples | |
|---|---|---|---|
| | Example 1 | A | B |
| Initial pentyl propionate solvent, g | 100.0 | 100.0 | 100.0 |
| Monomer Mixture, g(mol) | | | |
| Preparation A hydroxyalkyl methacrylate | 120.0(0.56) | — | — |
| Hydroxyethyl methacrylate | — | 72.9(0.56) | — |
| Hydroxypropyl methacrylate | — | — | 80.7(0.56) |
| Butyl acrylate | 90.0(0.62) | 113.1(0.78) | 109.5(0.75) |
| Methyl methacrylate | 90.0(0.90) | 114.0(1.14) | 108.5(1.09) |
| 3-Mercapto-1-propanol | 1.80 | 1.80 | 1.80 |
| Initiator Mixture, g | | | |
| Pentyl propionate | 62.7 | 62.7 | 62.7 |
| t-Amylperoxyacetate | 18.3 | 18.3 | 18.3 |
| Monomer Line Flush | | | |
| Pentyl propionate, g | 15.0 | 15.0 | 15.0 |
| Second Initiator Mixture, g | | | |
| Pentyl propionate | 15.0 | 15.0 | 15.0 |
| t-Amylperoxyacetate | 1.7 | 1.7 | 1.7 |
| Copolymer Properties | | | |
| Total Solids, % | 56.92 | 58.41 | 59.38 |
| $M_n$ | 2,383 | 2,778 | 3,191 |
| $M_w$ | 6,306 | 9,569 | 8,215 |
| $M_w/M_n$ | 2.64 | 3.44 | 2.57 |
| Viscosity, cP(°C.) | 630(20° C.) | 1,130(21° C.) | 1,190(21° C.) |

Example 2 and Control Example C. The copolymer-/oligomer of Example 1 and that of Control Example A were formulated into thermally-curable coating systems by weighing the ingredients identified below into glass containers, stirring well, and applying to 4-inch×6-inch Bonderite-952 steel panels using a 10-mil (254-micron) wet-clearance applicator. The coated panels were thermally cured in a 140° C. circulating-air oven for 30 minutes. Several panels of each coating system were prepared in this manner. The results indicated that the coating of Example 2 had improved hardness, crosshatch adhesion, and acid etch resistance at pH 3.0 in comparison to the coating of Control Example C.

|  | Example 2 | Control Example C |
|---|---|---|
| Ingredients, grams | | |
| Example 1 oligomer | 10.0 | — |
| Control Example A oligomer | — | 10.0 |
| Aminoplast 1 | 2.0 | 2.0 |
| Surfactant 1 | 0.16 | 0.16 |
| Surfactant 2 | 0.16 | 0.16 |
| Methyl amyl ketone solvent | 1.0 | 1.0 |
| Catalyst 1 | 0.05 | 0.05 |
| Cured Coating Properties | | |
| Film Thickness | 2.3 | 2.3 |
| Double rubs | >100 | >100 |
| 60° Gloss | 95.3 | 95.8 |
| 20° Gloss | 83.9 | 82.4 |
| Pencil hardness | 3H | 2H |
| Crosshatch adhesion | 5B | 4B |
| Impact resistance, in. lbs., forward/reverse | 40/2 | 40/2 |
| Acid etch resistance pH 2.0, 30 minutes, | | |
| at 50° C. | 4/4 | 3/3 |
| at 60° C. | 3/3 | 1/1 |
| Temperature first visible defect, °C. | 48/48 | 40/40 |
| Temperature first severe defect, °C. | 68/68 | 57/60 |
| Water spot test | 5/5 | 5/5 |

Example 3 and Control Example D. The copolymer-/oligomer of Example 1 and that of Control Example A were formulated into thermally-curable coating systems and applied a similar manner as in Example 2 and Control Example C except different amounts of catalyst and aminoplast were used. The coated panels were thermally cured at different (lower) temperatures than were used for Example 2 and Control Example C to determine the effect of cure temperature on properties. Cure time was 30 minutes. Several panels of each coating system were prepared in this manner. The results indicated that the coating of Example 3 had equivalent solvent resistance, equivalent or better hardness, and markedly improved acid-etch resistance than the coating of Control Example D.

|  | Example 3 | | Control Example D | |
|---|---|---|---|---|
| Ingredients, grams | | | | |
| Example 1 oligomer | 10.0 | | — | |
| Control Example A oligomer | — | | 10.0 | |
| Aminoplast 1 | 1.90 | | 1.95 | |
| Surfactant 1 | 0.16 | | 0.16 | |
| Surfactant 2 | 0.16 | | 0.16 | |
| Methyl amyl ketone solvent | 1.0 | | 1.0 | |
| Catalyst 1 | 0.31 | | 0.31 | |
| Cured Coating Properties | | | | |
| Cure temperature, °C. | 110 | 125 | 110 | 125 |
| Double rubs | >100 | >100 | >100 | >100 |
| Pencil hardness | F | H | F | F |
| Acid etch resistance pH = 2.0, 30 minutes | | | | |
| contact at 50° C. | 3/3 | 3/3 | 3/3 | 2/2 |
| at 60° C. | 1/2 | 2/2 | 1/2 | 1/1 |
| Temperature first visible defect, °C. | 47/47 | 50/50 | 45/48 | 49/49 |
| Temperature first severe defect, °C. | 60/62 | 65/65 | 60/62 | 53/53 |
| 10% acid, 15 minutes contact | | | | |
| at 50° C. | 5/5 | 5/5 | 5/5 | 5/5 |
| at 60° C. | 4/4 | 5/5 | 1/1 | 1/1 |
| Temperature first noticeable defect, °C. | 58/58 | 65/67 | 56/58 | 53/53 |
| Temperature first severe defect, °C. | 62/64 | 70/70 | 60/60 | 60/60 |

Example 4 and Control Example E. The copolymer-/oligomer of Example 1 and that of Control Example A were formulated into thermally-curable, isocyanate crosslinked coating systems by weighing the ingredients identified below into glass containers, stirring well, and applying to 4-inch×6-inch Bonderite-952 steel panels using a 10-mil (254-micron) wet-clearance applicator. The coated panels were thermally cured in a 140° C. circulating-air oven for 45 minutes. Several panels of each coating system were prepared in this manner. The results indicated that the coating of Example 4 had improved adhesion, 60° gloss, 20° gloss and improved or equivalent acid etch resistance at pH 2.0 than the coating of Control Example E.

|  | Example 4 | Control Example E |
|---|---|---|
| Ingredients, grams | | |
| Example 1 oligomer | 10.0 | — |
| Control Example A oligomer | — | 10.0 |
| Blocked Isocyanate 1 | 5.0 | 5.0 |
| Surfactant 1 | 0.20 | 0.20 |
| Catalyst 2 | 0.20 | 0.20 |
| Methyl amyl ketone, solvent | 2.0 | 2.0 |
| Cured Coating Properties | | |
| Film Thickness | 1.7 | 1.6 |
| Double rubs | >100 | >100 |
| 60° Gloss | 97.6 | 82.7 |
| 20°Gloss | 75.8 | 55.6 |
| Pencil hardness | F | F-H |
| Crosshatch adhesion | 5B | 4B |
| Impact resistance, in. lbs., forward/reverse | 160/70 | 160/120 |
| Acid etch resistance pH = 2.0, 30 minutes contact | | |
| at 50° C. | 4/4 | 4/4 |
| at 60° C. | 3/3 | 2/3 |
| Temperature first visible defect, °C. | 53/54 | 50/50 |
| Temperature first severe defect, °C. | 64/65 | 64/64 |

Example 5. In a similar manner as described in Example 1, a copolymer/oligomer of higher viscosity was prepared by reacting 110.8 grams (0.52 moles) of Preparation A hydroxyalkyl methacrylate, 35.6 grams (0.25 moles) of butyl acrylate, and 53.6 grams (0.54 moles) of methyl methacrylate in 100 grams of pentyl propionate (solvent) and in the presence of 0.14 grams of 3-mercapto-1-propanol chain-transfer agent. The initiator feed was 6.7 grams of t-amyl peroxyacetate catalyst in 63.3 grams of solvent, the post initiator feed was 0.5 grams of chain transfer catalyst in 15 grams of solvent, and the monomer-line flush was 15 grams of solvent.

The resulting oligomer/polymer had a number average molecular weight of 2,991, a weight average molecular weight of 8,334, a polydispersity of 2.79, and a viscosity of 2,090 centipoise.

Example 6. In a similar manner as described in Example 5, a copolymer/oligomer was prepared by reacting 60.0 grams of styrene, 120.0 grams of Preparation A hydroxyalkyl methacrylate, 120.0 grams of 2-ethylhexyl methacrylate, 6.0 grams of methacrylic acid, and 1.80 grams of 3-mercapto-1-propanol in 95 grams of pentyl propionate (solvent). The initiator feed was 10 grams of t-amyl peroxyacetate catalyst in 70 grams of solvent, the post initiator feed was 0.9 grams of chain transfer catalyst in 15 grams of solvent, and the monomer-line flush was 15 grams of solvent.

The resulting oligomer/polymer had a number average molecular weight of 5,557, a weight average molecular weight of 11,342, a polydispersity of 2.04, and a viscosity of 738 centipoise.

Example 7 and Control Example F. Example 7 copolymer/oligomer was prepared from a 300-grams of a mixture of the Preparation A alkyl monomethacrylate mixture, vinyl pivalate, and vinyl 2-ethylhexanoate in the amounts described below. For comparison purposes, Control Example F was prepared from a mixture containing hydroxyethyl methacrylate, vinyl pivalate, and vinyl 2-ethylhexanoate. The copolymers were prepared in a similar manner as described in Example 1 except the quantities of materials indicated below were used, and the initiator was t-butyl peroxybenzoate. The results indicated that Example 7 copolymer prepared from Preparation A hydroxyalkyl methacrylate had a lower molecular weight and viscosity than that of Control Example F, properties which allow preparation of higher total solids coating formulations. The total solids of Control Example F oligomer were about 2% higher than those of Example 7 oligomer, which would have an effect on the measured viscosity difference.

|  | Example 7 | Control Example F |
|---|---|---|
| Inital pentyl propionate solvent, g | 100.0 | 100.0 |
| Monomer Mixture, g |  |  |
| Preparation A hydroxy-alkyl methacrylate | 60.0 | — |
| Hydroxyethyl methacrylate | — | 60.0 |
| Vinyl privalate | 180.0 | 180.0 |
| Vinyl 2-ethylhexanoate | 60.0 | 60.0 |
| 3-Mercapto-1-propanol | 0.29 | 1.74 |
| Initiator Mixture, g |  |  |
| Pentyl propionate | 70.0 | 70.0 |
| t-Butylperoxybenzoate | 11.0 | 11.0 |
| Monomer Line Flush |  |  |
| Pentyl propionate, g | 15.0 | 15.0 |
| Second Initiator Mixture, g |  |  |
| Pentyl propionate | 15.0 | 15.0 |
| t-Butylperoxybenzoate | 1.0 | 1.0 |
| Copolymer Properties |  |  |
| Total Solids, % | 60.84 | 62.66 |
| $M_n$ | 1,802 | 2,114 |
| $M_w$ | 4,892 | 5,027 |
| $M_w/M_n$ | 2.71 | *2.38 |
| Viscosity, cP | 183 | 260 |

Examples 8, 9 and 10 and Control Examples G and H. The copolymer/oligomer of Example 7 and that of Control Example F were formulated into thermally-curable, aminoplast crosslinked coating systems by weighing the ingredients described below into glass containers, stirring well, and applying to 4-inch×6-inch Bonderite-952 steel panels using a 10-mil (254-micron) wet-clearance applicator. Before using for formulation, the Control Example F oligomer was concentrated to a total solids of 79.3% by weight by removal of pentyl propionate solvent. The coated panels were thermally cured in a 140° C. circulating air oven for 30 minutes. Several panels of each coating system were prepared in this manner.

| | Examples and Control Examples | | | | |
|---|---|---|---|---|---|
| | 8 | G | 9 | 10 | H |
| Ingredients, grams | | | | | |
| Example 9 oligomer | 10.0 | — | 10.0 | 10.0 | — |
| Control Example H oligomer | — | 10.0 | — | — | 10.0 |
| Aminoplast 1 | 0.60 | 2.07 | — | — | — |
| Aminoplast 2 | — | — | 1.41 | 2.0 | 2.0 |
| Surfactant 1 | 0.13 | 0.20 | 0.16 | 0.16 | 0.16 |
| Surfactant 2 | 0.14 | 0.20 | 0.16 | 0.16 | 0.16 |
| Catalyst 1 | 0.14 | 0.32 | 0.05 | 0.05 | 0.05 |
| Methyl amyl ketone, solvent | — | 2.5 | — | — | — |
| Oligomer hydroxyl to aminoplast alkyloxy molar ratio | 1/2.74 | 1/2.74 | 1/2.74 | 1/3.97 | 1/2.4 |
| Cured Coating Properties | | | | | |
| Film Thickness | 2.5 | 2.3 | 2.2 | 2.5 | 2.1 |
| Double rubs | 100 | >100 | >100 | >100 | >100 |
| 60° Gloss | 86.7 | 96.4 | 96.2 | 97.1 | 93.9 |
| 20° Gloss | 74.1 | 84.6 | 79.4 | 84.9 | 79.7 |
| Pencil hardness | 2B | H | HB | F | F |
| Crosshatch adhesion | 1B | 4B | 5B | 5B | 4B–5B |
| Impact resistance in. lbs., forward/reverse | 4/2 | 40/2 | 30/2 | 40/2 | 40/2 |
| Acid etch resistance pH = 2.0, 30 minutes contact | | | | | |
| at 50° C. | 4/4 | 3/3 | 5/5 | 3/3 | 1/1+ |
| at 60° C. | 2/1 | 1/1 | 3/3 | 1/1 | 1/1 |
| Temperature first visible defect, °C. | 45/47 | 45/48 | 52/52 | 50/50 | 50/50 |
| Temperature first severe defect, °C. | 62/60 | 60/60 | 66/66 | 58/60 | 50/50 |
| 10% acid, 15 minutes contact | | | | | |
| at 50° C. | 5/5 | 5/5 | 5/5 | 5/5 | 5/5 |
| at 60° C. | 4/4 | 1/1+ | 4/4 | 5/5 | 4/4 |
| Temperature first visible defect, °C. | 60/60 | 55/55 | 60/62 | 62/64 | 62/62 |
| Temperature first severe defect, °C. | 64/64 | 58/58 | 70/70 | 70/70 | 65/65 |

+Coating was cut through to bare steel, i.e., very severe attack.

Example 11. A 4-necked glass reactor is equipped with a stirrer, temperature-measuring device, gas sparge, condenser, and a feeding port. Two moles (228 grams) of e-caprolactone are added to the reactor and heated to and held at 100° C. for 30 minutes while sparging with dry nitrogen. The temperature is then increased to 130° C. and the sparge is changed to dry air. Then, one mole (214 grams) of the Preparation A methacrylate ester is added along with 500 parts per million of the monomethylether of hydroquinone and 50 parts per million of stannous octanoate. The reaction mass is held at 130°–135° C. for 6 hours after which time it is cooled to room temperature. This caprolactone acrylate is stored for future use.

Example 12. One hundred grams (0.226 moles or equivalents) of the caprolactone acrylate of Example 11 is placed in the Example 11 reactor and heated to 45° C. while maintaining an air sparge. Then 29.6 grams (0.113 moles or 0.226 equivalents) of 4,4'-dicyclohexylmethyl diisocyanate are added. A small exotherm is noted. The reaction is allowed to proceed at 45° C.–50° C. for 10 hours after which time the urethane acrylate reaction product is cooled to room temperature and stored with an air blanket for later use in radiation-cure formulations.

Example 13. One hundred grams (0.467 moles or equivalents) of the Preparation A methacrylate ester are placed in the Example 11 reactor. The acrylate ester is heated to 45° C. while maintaining an air sparge. Then 61.2 grams (0.234 moles or 0.467 equivalents) of 4,4'-dicyclohexylmethyl diisocyanate are added. A small exotherm is noted. The reaction is allowed to proceed at 45° C.–50° C. for 10 hours after which time the urethane acrylate reaction product is cooled to room temperature and stored with an air blanket for later use in radiation-cure formulations.

Example 14. To an amber-colored glass container, 20 grams of the acrylic oligomer of Example 1, 40 grams of 3,4-epoxycyclohexyl 3,4-epoxycyclohexane carboxylate, and 1.8 grams of Photoinitiator 1 are added. The ingredients are well mixed and then applied to a steel panel by the draw-down method. The coated panel is then placed on a conveyor moving at 30 feet/minute and passing under a 300 watt-per-inch medium-pressure mercury vapor lamp to effect cure. A tack-free, clear coating results.

Example 15. Ten grams of the acrylate oligomer of Example 5, 30 grams of 3,4-epoxycyclohexyl 3,4-epoxycyclohexane carboxylate, 1.5 grams of diethylammonium triflate catalyst, and 5 grams of methyl amyl ketone solvent are added to a glass container and well mixed. The mixture is coated onto a steel panel with a No. 22 wire-wound rod. The coated panel is allowed to air dry for 10 minutes and then it is oven baked at 115° C. for 20 minutes. A clear, tack-free coating with good water resistance results.

Example 16. In a similar manner as described in Example 5, a copolymer/oligomer was prepared by placing 100 grams of pentyl propionate in the reactor and adding 100.50 grams of isodecyl methacrylate, 115 grams of the Preparation A hydroxyalkyl acrylate, about 5 grams of a diacrylate with the following structure,

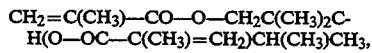

CH$_2$=C(CH$_3$)—CO—O—CH$_2$C(CH$_3$)$_2$C-H(O—OC—C(CH$_3$)=CH$_2$)CH(CH$_3$)CH$_3$, 73.50 grams of isobornyl methacrylate, 6 grams of methacrylic acid, and 0.21 grams of 3-mercapto-1-propanol. The initiator feed was composed of 10 grams of t-amyl peroxyacetate dissolved in 70 grams of pentyl propionate, the post initiator feed was composed of 0.9 grams of t-amyl peroxyacetate dissolved in 15 grams of pentyl propionate, and the monomer line flush was 15 grams of pentyl propionate. The resulting polymer had a Brookfield viscosity of 715 cP at a total solids content of 54.58%, which indicated it would be useful for preparing high solids coatings.

Examples 17 and 18. These copolymers were prepared from a 300-gram mixture of a Preparation A alkyl monomethacrylate mixture, and other copolymerizable ethylenically unsaturated monomers as indicated below. The initial butyl propionate solvent was placed in a 2-liter, four-neck, glass reaction flask equipped with a mechanical stirrer, a Thermo-watch heat controller, a nitrogen sparger, a water-cooled condenser, and 500-milliliter and 125-milliliter addition funnels. A nitrogen sparge was maintained throughout the procedure. The solvent was heated to 140° C., and the monomer mixture was fed by means of a piston pump to the flask over a four-hour period while controlling the temperature at 140° C. Concurrently, the initiator mixture consisting of t-amyl peroxyacetate initiator dissolved in butyl propionate was fed to the reaction flask by a second piston pump over the same time period. The two feeds were introduced into the reactor below the liquid surface and from opposite sides of the reactor. After completion of the feeding step, the monomer line was flushed with 15 g butyl propionate and the reaction was allowed to proceed for 30 minutes at 140° C. Then a second initiator feed consisting of a mixture of 2,5-dimethyl-2,5-di(2-ethylhexanoylperoxy)hexane dissolved in butyl propionate was fed to the reaction mass and the reaction was allowed to proceed for an additional 2 hours at 140° C. The solution of copolymer was then cooled to room temperature and analyzed by gel permeation chromatography using polystyrene standards to determine relative average molecular weights, for total solids content, and for viscosity. In each case, low viscosity products that were useful in coating formulations were prepared.

|  | Examples | |
| --- | --- | --- |
|  | 17 | 18 |
| Inital butyl propionate solvent, g | 100.0 | 100.0 |
| Monomer Mixture, g(mol) | | |
| Preparation A hydroxyalkylacrylate | 120.0 | 120.0 |
| Lauryl methacrylate | 105.0 | 105.0 |
| t-Butyl methacrylate | 69.0 | — |
| Methyl methacrylate | — | 69.0 |
| Methacrylic acid | 6.0 | 6.0 |
| Initiator Mixture, g | | |
| Butyl propionate | 70.0 | 70.0 |
| t-Amylperoxyacetate* | 10.0 | 10.0 |
| Monomer Line Flush | | |
| Pentyl propionate, g | 15.0 | 15.0 |
| Second Initiator Mixture, g | | |
| Pentyl propionate | 15.0 | 15.0 |
| 2,5-Dimethyl-2,5-di(2-ethyl hexanoylperoxy)hexane** | 0.9 | 0.9 |
| Copolymer Properties | | |
| Total Solids, % | 55.1 | 56.7 |
| M$_n$ | 4528 | 5397 |
| M$_w$ | 9285 | 10,620 |
| M$_w$/M$_n$ | 20.5 | 1.97 |
| Viscosity+, cP, 25° C. | 299 | 717 |

*Lupersol 555M60(60TS)
**Lupersol 256
+ Brookfield viscosity

Example 19. The copolymer of Example 18 is reacted with butyl isocyanate using 75% of the moles of butyl isocyanate required for reaction with the available hydroxyl groups on the polymer. The butyl isocyanate is slowly added to the copolymer in a suitable enclosed reactor equipped with a stirrer and other conventional equipment at room temperature over a 30-minute time period. The reaction mass undergoes a mild exotherm shortly after the addition. After 8 hours, infrared analysis is used to analyze the reaction mass. The reaction is continued until the butyl isocyanate is reduced to a desired level. The modified polymer containing N-butyl carbamoyloxyalkanoyoxyalkyl groups is stripped of any residual isocyanate and then stored for future use as an intermediate in preparing coating compositions.

Example 20. Fifty grams (0.233 moles or equivalents) of the Preparation A methacrylate ester are placed in a reactor equipped with a stirrer, feeding port, and means of temperature measurement and control. The methacrylate ester is heated to 80° C. and 0.23 equivalents of phthalic anhydride are slowly added. The temperature is then increased to 120° C. and held there for 2 hours after which time the reaction mass is cooled to room temperature and stored for future use.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

We claim:

1. A compound selected from the group consisting of 2-ethyl-3-hydroxyhexyl methacrylate, 1-propyl-2-ethyl-3-hydroxypropyl methacrylate, 1-ethyl-2-methyl-3-hydroxypropyl methacrylate, 2-methyl-3-hydroxypentyl methacrylate, 2-propyl-3-hydroxyheptyl methacrylate, 1-butyl-2-propyl-3-hydroxypropyl methacrylate, 2-ethyl-3-hydroxyheptyl methacrylate, 1-butyl-2-ethyl-3-hydroxypropyl methacrylate, 2-propyl-3-hydroxypropyl methacrylate, 2-ethyl-3-hydroxypropyl methacrylate, 1-i-butyl-2-i-propyl-3-hydroxypropyl methacrylate, 2-i-propyl-3-hydroxy-5-methylhexyl methacrylate, 1-methyl-2-i-propyl-3-hydroxypropyl methacrylate, 2-i-propyl-3-methyl-3-hydroxypropyl acrylate, 1-i-butyl-3-hydroxypropyl methacrylate, 3-hydroxy-5-methylhexyl methacrylate, 1-methyl-2-butyl-3-hydroxypropyl methacrylate, 2-butyl-3-hydroxybutyl methacrylate, 1-i-propyl-2,2-dimethyl-3-hydroxypropyl methacrylate, and 2,2-dimethyl-3-hydroxy-4-methylpentyl methacrylate.

* * * * *